United States Patent [19]
Stevens-Wright et al.

[11] Patent Number: 5,715,817
[45] Date of Patent: Feb. 10, 1998

[54] BIDIRECTIONAL STEERING CATHETER

[75] Inventors: Debbie E. Stevens-Wright, N. Andover; John R. Fagan, Pepperell; Dino F. Cuscuna, Reading; Sarkis Karakozian, Belmont, all of Mass.

[73] Assignee: C.R. Bard, Inc., Murray Hill, N.J.

[21] Appl. No.: 478,206

[22] Filed: Jun. 7, 1995

Related U.S. Application Data

[63] Continuation-in-part of Ser. No. 84,549, Jun. 29, 1993, Pat. No. 5,462,527.

[51] Int. Cl.⁶ .............................. A61B 5/042; A61N 1/05
[52] U.S. Cl. .............................. 128/642; 604/95; 606/41; 607/122
[58] Field of Search .......................... 128/642; 607/122; 604/95; 606/41

[56] References Cited

U.S. PATENT DOCUMENTS

| | | |
|---|---|---|
| 3,270,641 | 9/1966 | Gosselin . |
| 3,470,876 | 10/1969 | Barchilon . |
| 3,552,384 | 1/1971 | Pierie et al. . |
| 3,557,780 | 1/1971 | Sato . |
| 4,007,646 | 2/1977 | De Jonge . |
| 4,078,555 | 3/1978 | Takahashi . |
| 4,586,923 | 5/1986 | Gould et al. . |
| 4,688,554 | 8/1987 | Habib . |
| 4,781,185 | 11/1988 | Kauphusman et al. . |
| 4,784,117 | 11/1988 | Miyazaki . |
| 4,784,463 | 11/1988 | Miyazaki . |
| 4,799,496 | 1/1989 | Hargreaves et al. . |
| 4,826,087 | 5/1989 | Chinery . |
| 4,838,859 | 6/1989 | Strassman . |
| 4,860,757 | 8/1989 | Lynch et al. . |
| 4,873,965 | 10/1989 | Danieli . |
| 4,874,371 | 10/1989 | Comben et al. . |
| 4,917,094 | 4/1990 | Lynch et al. . |
| 4,976,688 | 12/1990 | Rosenblum . |
| 4,996,974 | 3/1991 | Ciarlei . |
| 4,998,917 | 3/1991 | Gaiser et al. . |
| 5,125,895 | 6/1992 | Buchbinder et al. . |
| 5,125,896 | 6/1992 | Hojeibane . |
| 5,179,935 | 1/1993 | Miyagi . |
| 5,195,968 | 3/1993 | Lundquist et al. . |
| 5,199,950 | 4/1993 | Schmitt et al. . |
| 5,325,845 | 7/1994 | Adair . |
| 5,344,397 | 9/1994 | Heaven et al. . |
| 5,383,852 | 1/1995 | Stevens-Wright . |
| 5,462,527 | 10/1995 | Stevens-Wright et al. ............... 604/95 |
| 5,478,330 | 12/1995 | Imran et al. ............................ 604/282 |

FOREIGN PATENT DOCUMENTS

| | | |
|---|---|---|
| 0 521 595 | 10/1984 | European Pat. Off. . |
| 0 616 794 A1 | 9/1994 | European Pat. Off. . |
| 2138687 | 10/1984 | United Kingdom . |
| WO 91/11213 | 8/1991 | WIPO . |
| WO 93/20878 | 10/1993 | WIPO . |
| WO 94/11057 | 5/1994 | WIPO . |

*Primary Examiner*—Lee S. Cohen
*Attorney, Agent, or Firm*—Darby & Darby

[57] ABSTRACT

A bidirectional steering catheter comprising a distal electrode assembly, a flexible tip assembly, an elongated shaft having a central lumen running the length of the shaft, and a handle/actuator. A plurality of ring electrodes are attached to the surface of the flexible tip assembly. Signal wires running the length of the catheter are electrically connected to each ring electrode. At least two pull cables having first and second ends extend distally through the central lumen. The first end of each pull cable is attached to the handle/actuator. The second end of each pull cable is attached to the distal electrode assembly, such that the distal electrode assembly may be moved between a first and a second position within a single plane by manipulating the handle/actuator. At least two reinforcement members are located inside the flexible tip assembly. Each reinforcement member has a proximal section, a middle section and a distal section. Each proximal section has a larger diameter than each middle section, thus being stiffer than the middle section. This variable stiffness along the length of the each reinforcement member distributes stresses evenly along the length of the tip assembly.

25 Claims, 7 Drawing Sheets

BIDIRECTIONAL STEERING CATHETER

This is a continuation-in-part of U.S. patent application Ser. No. 08/084,549, filed on Jun. 29, 1993, now U.S. Pat. No. 5,462,507, and incorporated by reference herein.

This invention relates to steerable catheters. More particularly, this invention relates to a catheter of the type used for endocardial catheter recording, having a selectively reinforced flexible tip assembly.

FIELD OF THE INVENTION

The clinical role of endocardial catheter recording is to direct ablation, surgical, and drug therapies in the treatment of supraventricular tachycardia, ventricular tachycardia, atrial flutter, atrial fibrillation and other arrhythmias. The success and advancement of current therapies is dependent upon the development and use of more precise localization techniques which will allow accurate anatomical determination of arrhythmogenic sites. Historically, the electrophysiologist has had to compromise between placing the catheter in the place of clinical interest and areas which are anatomically accessible.

Prior art catheter placement has been restricted generally to areas which can be repeatedly accessed by the electrophysiologist. These areas include the HRA (high right atrium), the RVA (right ventricular apex), the coronary sinus and the HIS bundle. To obtain meaningful information about arrhythmogenic sites and reentry circuits with catheters it is imperative that the range of reproducible catheter placement sites be expanded and the number of electrograms recorded over a given area be increased. Some of these additional sites include atrial sites above the tricuspid and mitral valves, ventricular sites circumferential to the mitral and tricuspid valve leaflets, distal areas of the coronary sinus and great cardiac vein, the AV nodal area and the left ventricle, to name a few.

One area of advancement in improving localization techniques and accessing additional recording sites includes the use of steerable catheters. One type of prior art steerable catheter offers improved maneuverability to specific, otherwise inaccessible sites by providing catheters shaped specifically to access a particular site. Although perhaps useful for some less inaccessible sites, the use of this type of catheter is limited, not very practical, and not helpful in reaching sites requiring active articulation during placement. Three such preshaped catheters are described in U.S. Pat. No. 3,503,385 issued to Stevens, U.S. Pat. No. 3,729,008 issued to Berkovits, and U.S. Pat. No 4,860,769 issued to Forgerty.

Another type of prior art steerable catheter attempts to improve placement maneuverability by providing catheters having deflecting tips. These catheters include a soft and flexible distal portion of a certain length attached to a proximal shaft made from a stiffer material. The tip may be selectively deflected but only in a prescribed arc, i.e., the tip bends in one planar direction. Examples of deflecting tip catheters are described in U.S. Pat. No. 4,920,980 issued to Jackowski, U.S. Pat. No. 4,960,411 issued to Buchbinder, and U.S. Pat. No. 4,960,134 issued to Webster.

The main disadvantage of the above-described preformed and deflecting tip type catheters is that the tip of the catheter in each case may be steered only in a prescribed manner which cannot be altered during its placement. This restriction of steering of these types of prior art catheters limits their effectiveness in reaching many of the desired recording sites.

Many of the desired sites require that the catheter traverse paths having many sharp bends and be able to negotiate multiple changes of direction through any or all of the three perpendicular planes of movement. Four-way steerable catheters have been developed in an attempt to provide a catheter with the above-described multi-planar maneuverability. As examples, such four-way steerable catheters are described in U.S. Pat. No. 3,470,876 issued to Barchilon, and U.S. Pat. Nos. 4,921,482, 4,998,916 and U.S. Pat. No. 5,037,391 issued to Hammerslag.

U.S. Pat. No. 5,383,852 entitled Catheter With Independent Proximal and Distal Control issued to Stevens-Wright discloses a catheter capable of bending proximal and distal sections of the catheter tip assembly by applying tension selectively to four pull cables. The actuator mechanism for the pull cables is supported in a handle which is manipulated by the physician to control the bending of the tip assembly. The handle requires separate controls for proximal and distal bending, respectively. As is customary, the entire handle may be rotated during use to apply a torquing force to the catheter; therefore, the individual controls should be easily accessible and recognizable when the handle is rotated. All required manipulations should be consistent regardless of the position of the handle or its placement.

The tip reinforcement methods employed in current catheter designs use stainless steel materials. One disadvantage of using stainless steel is that the catheter requires a high actuating force to bend to small radius curves. Another disadvantage is that the presently employed steerable catheters allow the reinforcement material to move away from the neutral axis during actuation. This causes the reinforcement material to be placed in tension when it moves above the neutral axis, and to be placed in compression when it moves below the neutral axis. This displacement results in a jerky, non-uniform tip motion.

Further, steerable catheters having actuating cables that extend along the length of the catheter tend to have high shear forces within the proximal region of the tip assembly and are subject to compressive loading as well as bending loads. The compressive loads cause the tip to shorten after actuation.

OBJECTIONS OF THE INVENTION

The object of the invention is to provide a catheter which exhibits minimal forces when actuated to small radius curves, and lower actuation strokes.

A further object of the invention is to provide a catheter which evenly distributes the stresses along the length of the tip assembly and, thereby minimize the shear forces to the proximal region of the catheter tip.

A still further object of the invention is to provide a catheter in which the material characteristics of the reinforcement determine the tip motion.

Another object of the invention is to provide a catheter capable of uniform tip motion throughout the entire electrophysiology procedure, such that performance is not deteriorated or subject to material temporal dependencies.

Yet another object of the invention is to provide a catheter capable of smooth tip motion as a result of the reinforcement not migrating away from the neutral axis.

Still another object of the invention is to improve planarity by preventing twisting within the distal portion of the catheter.

SUMMARY OF THE INVENTION

A bidirectional steering catheter according to the invention includes a distal electrode assembly attached to the distal portion of a flexible tip assembly, an elongated shaft, and a handle/actuator. According to the invention, the reinforcement members are provided within the reinforcement lumens embedded within the flexible tip assembly. These members are preferably made from Nitinol, a Nickel-Titanium alloy. Each reinforcement member is divided into a distal section, a middle section and a proximal section. The proximal section is of greater stiffness than the middle section. The distal section assures radial alignment of the reinforcement members along the lengths thereof. The variable stiffness along the length of the reinforcement members distributes the stresses evenly along the length of the tip assembly, thus minimizing the shear forces proximally. This results in a near constant bending moment, that leads to lower forces to actuate and lower actuation strokes.

In the preferred embodiment, a handle/actuator is connected to two pull cables which run through the length of the shaft and tip assemblies. The distal ends of the pull cables are adhesively attached to the distal tip of the catheter electrode assembly. Each pull cable is encapsulated within a TEFLON sheath. By manipulating the slider control, a physician can selectively apply tension to any one of the two pull cables to enable bidirectional control of the catheter tip assembly.

DETAILED DESCRIPTION OF THE PREFERRED EMBODIMENT

Figure 1:
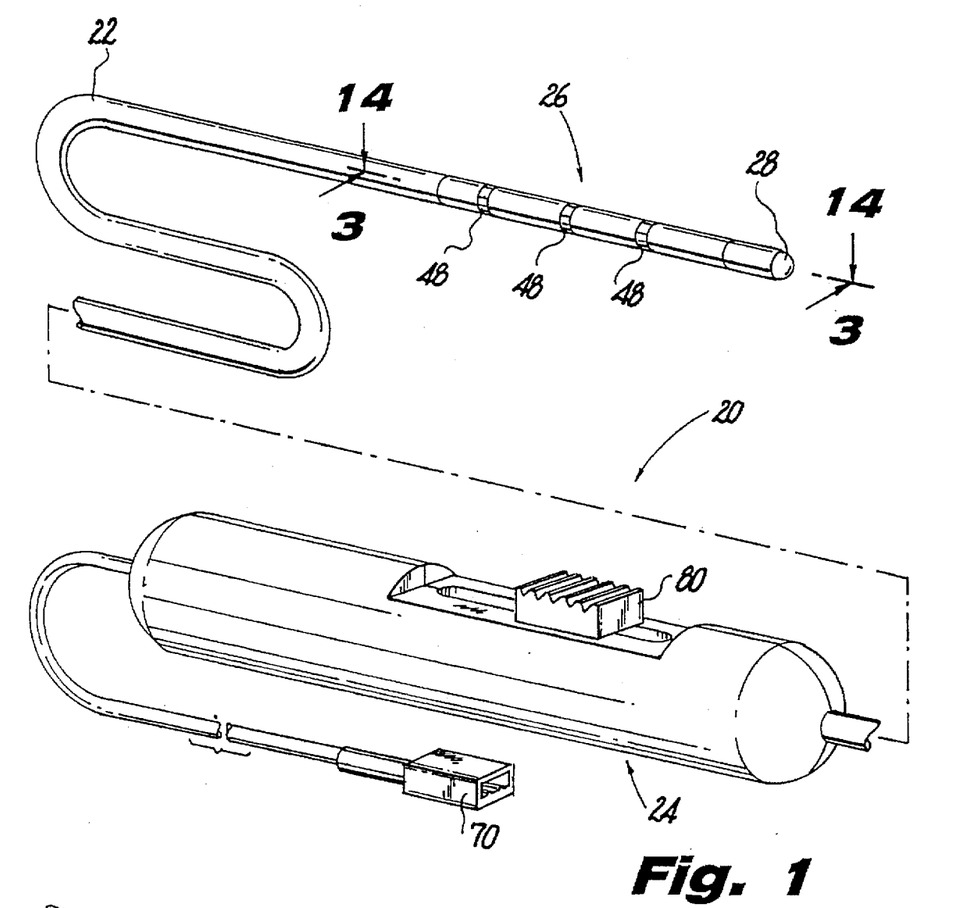
FIG. 1 is a perspective view of a steerable catheter according to the invention.

A preferred embodiment of a bidirectional steerable electrode catheter 20 comprises an flexible elongated shaft 22, a handle/actuator 24, a flexible tip assembly 26, and a distal electrode assembly 28 (FIG. 1).

Referring to FIGS. 3–8, the elongated shaft 22 extends distally from the handle/actuator 24 to the flexible tip assembly 26. The elongated shaft 22 surrounds a coaxial spring 30 which extends the length of the shaft 22. The coaxial spring 30 is enclosed within a flexible outer protective sheath 32. The coaxial spring 30 encloses a central lumen 40 which runs axially through the center of the elongated shaft 22. The coaxial spring 30 is fixed axially within the shaft 22 between two spring stops 34a and b. The spring stops 34a and b serve to anchor the spring 30 within the elongated shaft 22, and thereby prevent any longitudinal movement within the shaft 22. The distal spring stop 34b is tapered outwards, such that the thickness of the distal spring stop 34b decreases from its proximal to distal end. This outward tapering, in effect, increases the size of the central lumen 40 between the elongated shaft 22 and the flexible tip assembly 26.

Figure 7:
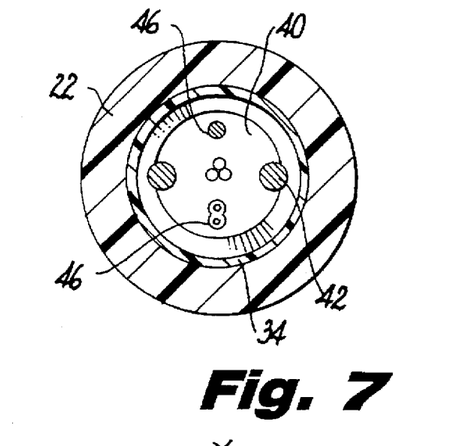
Figure 8:
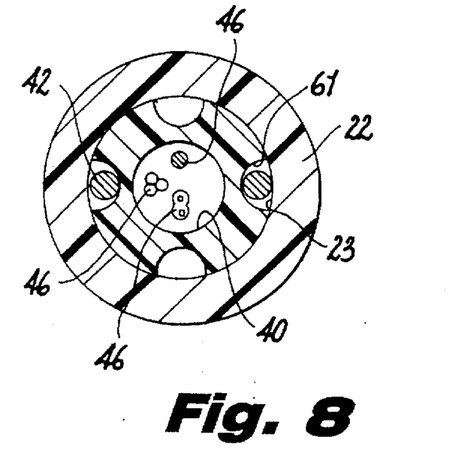
Figure 9:
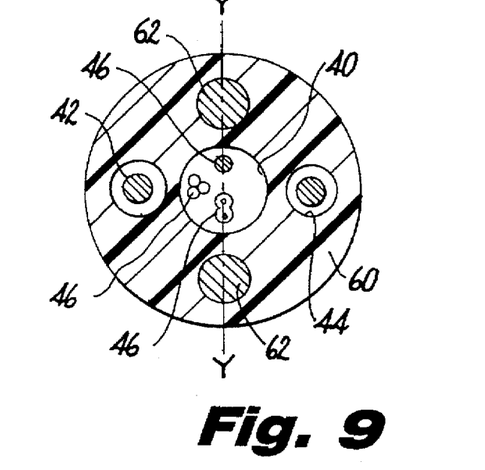

Within the central lumen 40 are two pull cables 42 that extend distally from the handle/actuator 24 into the distal electrode assembly 28 of the catheter 20. The two pull cables 42 run radially along opposite inner walls of spring 30, and the distal spring stop 34b, thus following the outward taper of the inner surface of the distal spring stop 34b (FIG. 7). This serves to lead the putt cables 42 into their respective pull cable lumens 44, as illustrated by FIGS. 8 and 9. The pull cables 42 then extend distally to a location within the distal electrode assembly 28 the catheter 20. The distal ends of the pull cables 42 are adhesively attached within the distal electrode assembly 28. Thus, the pull cables 42 translate handle/actuator 24 manipulation by the working electrophysiologist through the length of the shaft 22 into bidirectional, single planar, bending movement of the tip assembly 26 as described below.

Also included within the central lumen 40 are a plurality of signal wires 46 which allow electrical communication between a plurality of ring electrodes 48, the distal electrode cap 50, and the thermistor 52.

The flexible tip assembly 26 (FIGS. 3, 9–12, and 14) is attached to the distal end of the elongated shaft 22, and comprises a tubular section 60, two reinforcement members 62, a plurality of ring electrodes 48, and signal wires 46. The tubular section 60 extends distally from approximately 4 mm within the elongated shaft 22 to the distal electrode assembly 28. Embedded within the tubular section 60 are two reinforcement lumens 64 housing the two reinforcement members 62, respectively, and two pull cable lumens 44 also housing the two pull cables 42, respectively. A plurality of ring electrodes 48 are spaced apart along the periphery of the flexible tip assembly 26. The central lumen 40 extends through the center of the tubular section 60 and contains the signal wires 46. The tubular section 60 is aligned coaxially with the elongated shaft 22.

Figure 3:
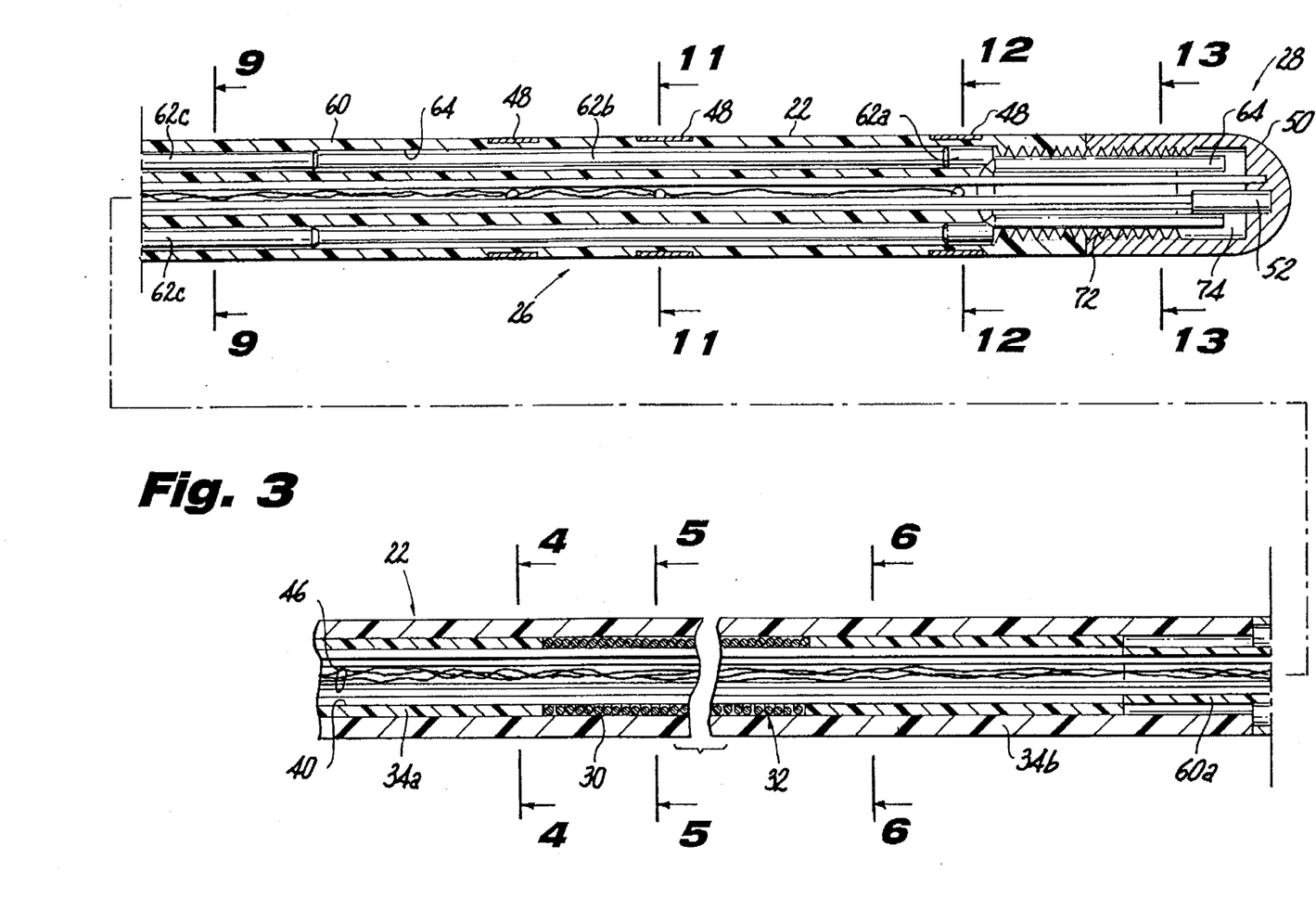
FIG. 3 is a longitudinal section along the line 3—3 of FIG. 1, cut along the reinforcement lumens.

As shown in FIGS. 3, and 9–12, the two reinforcement members 62 occupy the two reinforcement lumens 64 on a vertical axis y—y (FIG.9) through the center of the catheter 22. The reinforcement members 62 extend distally through the flexible tip assembly 26 (FIG. 3). According to the invention, the reinforcement members 62 have a distal section 62a, a middle section 62b, and a proximal section 62c (FIG. 3). In a preferred embodiment of the invention, the distal section 62a and the proximal section 62c are 0.015 inch in diameter. The middle section 62b is 0.010 inch in diameter. Preferably, both the proximal section 62c and distal section 62a are of substantially the same diameter as the inner diameter of the lumen, thereby resulting in a "snug" fit within the reinforcement lumen 64. The proximal section 62c has a greater diameter that the middle section 62b, thereby imparting greater stiffness to the proximal reaction of the flexible tip assembly 26. This variable stiffness reinforcement allows stresses to be evenly distributed along the length of the flexible distal tip assembly 26 by relieving stresses in the proximal section when the tip is being manipulated by the user. Typically, without the variable reinforcement, the tip assembly displays a D-shaped bending curve, indicating that the proximal section of the tip assembly 26 is under greater stresses than the middle and distal sections, in the form of higher shear forces and greater compressive and bending loads. By stiffening the proximal section 62c, a more circular, "pure bending" curve is achieved, thus indicating an evenly distributed stress pattern along the length of the flexible tip assembly. This (1) minimizes the shear forces in the proximal section, (2) leads to lower actuation forces, and (3) leads to shorter actuation strokes.

The distal section 62a of the reinforcement member is anchored to the tubular section 60. This assures radial alignment of the reinforcement member 62 along the length of the reinforcement lumens 64. In other words, the mid-line of each reinforcement member 62 remains aligned with the neutral axis plane. Were the distal section 62a not anchored to the tubular section 60, the reinforcement member 62 would tend to float within the reinforcement lumen 64, either above or below the neutral axis. This would allow the portions of the reinforcement member 62 above the neutral axis to be placed in tension, while, at the same time, subjecting those portions of the reinforcement member 62 below the neutral axis to compression. This tends to result in "jerky," non-uniform tip motion. The use of the distal radial alignment sections prevents movement away from the neutral axis, and provides smooth consistent tip movement.

The middle section 62b of the reinforcement member 62 has a smaller diameter than the proximal and distal sections 62c and a. The proximal section 62c and the middle sections 62b are illustrated as having constant diameters, respectively (FIG. 3). However, in an alternative embodiment, both the proximal section 62c and the middle section 62b may be tapered along their length. Such tapering will be dictated by the stiffness required in the flexible tip assembly 26.

According to the invention, the reinforcement members 62 are made from Nitinol, a Nickel-Titanium alloy. However, other super-elastic alloys may be used. The advantage of using Nitinol or another super-elastic alloy is that they possess a hysteritic stress/strain curve that exhibits an elastic plateau at a given stress value. Therefore, as the tip assembly 26 is placed under strains of between 2–8 percent of its length, the stresses do not increase correspondingly with the strain, but remain constant. This results in lower actuation forces. Further, because the reinforcement member 62 provides a bending stiffness that is a significant percentage of the total tip stiffness, this higher stiffness ratio between the reinforcement member 62 and the tip extrusion allows the tip motion to be dictated primarily by the material characteristics of the reinforcement member 62, as opposed to the material characteristics of the deformable plastic tubular section 60. As such, the tip displays (1) minimum time/temperature rate effects that are present with plastics, (2) faster recovery to non-deformed position, and (3) minimal "creep."

By employing the variable diameter reinforcement members 62a–c, the increased bending stiffness in the proximal section improves planarity by offering bias in one axis of bending without accentuating material inconsistencies along the entire length of the catheter.

Figure 12:
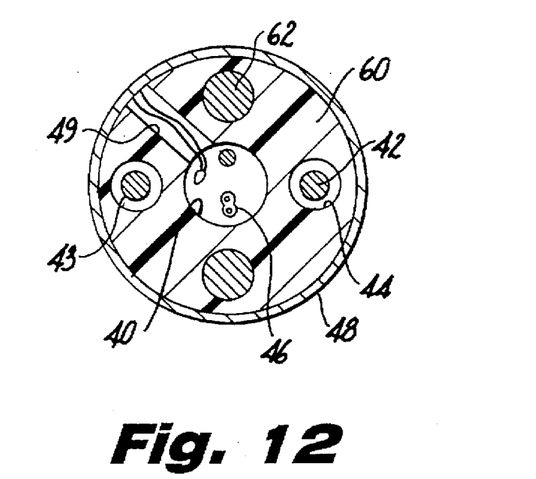
Figure 13:
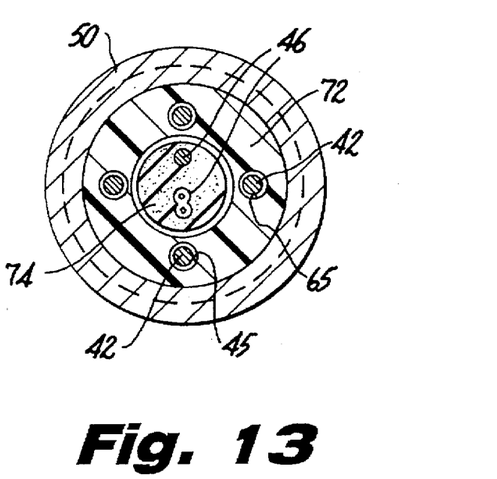
Figure 14:
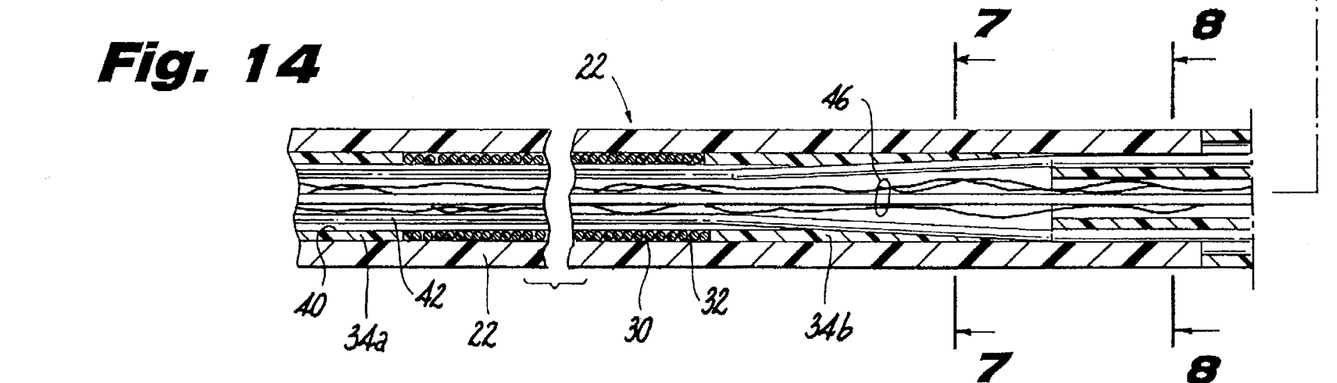
FIG. 14 is a longitudinal section along the line 14—14 of FIG. 1, cut along the pull wire lumens.
Figure 15A:
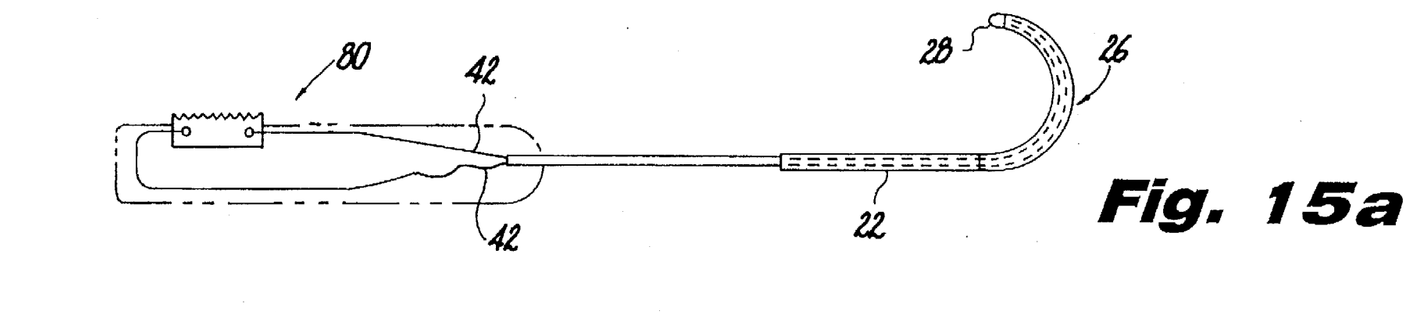
FIGS. 15a–c illustrate the slider mechanism used to bend the tip assembly in a single plane.
Figure 15B:
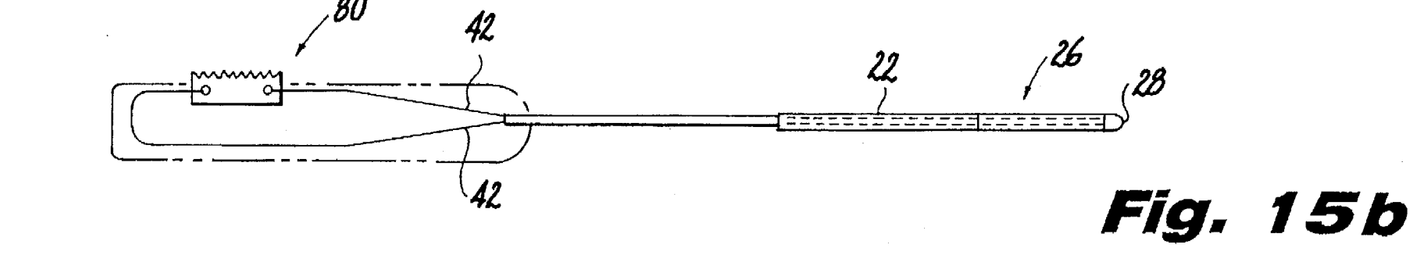
Figure 15C:
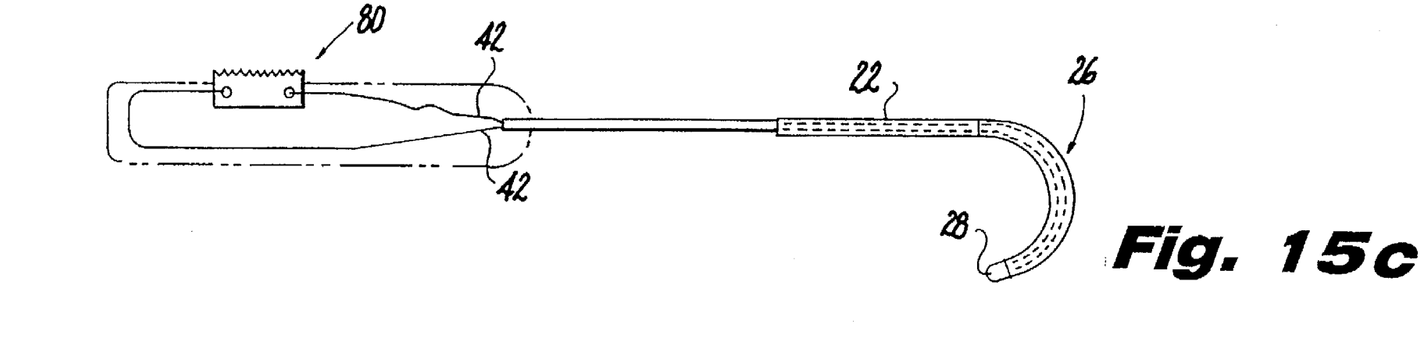

On a horizontal axis, x—x (FIG. 10) lying perpendicular to the vertical axis y—y containing the reinforcement lumens 64, are the two pull cable lumens 44 (FIG. 14). The pull cable lumens are initially formed within the elongated shaft 22, between the outer surface of the tubular section 61 and the inner surface 23 of the elongated shaft 22. The two pull cable lumens 44 continue axially through the flexible tip portion 26. The pull cable lumens 44 house the two pull cables 42, respectively. As shown in FIGS. 4–14, the cable lumens are placed as close as possible to the circumference of the flexible tip assembly 26. Each pull cable 42 is further enclosed in a TEFLON sheath 43.

Figure 2:
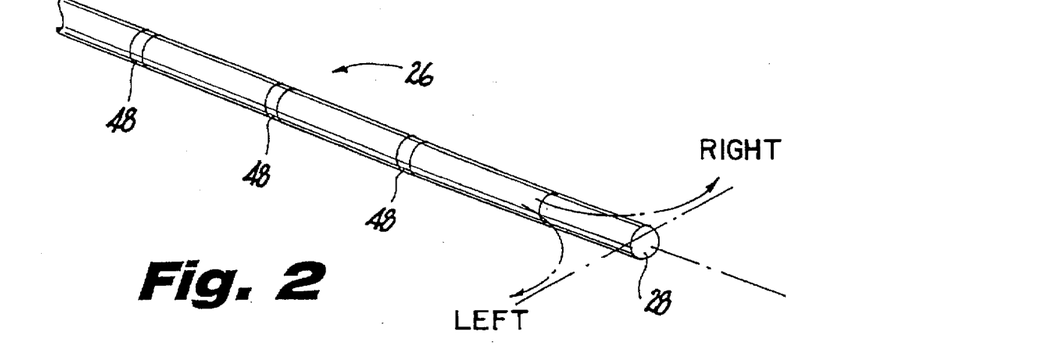
FIG. 2 is a diagrammatic perspective view of a tip assembly of the catheter showing the tip assembly bending in one plane.
Figure 2A:
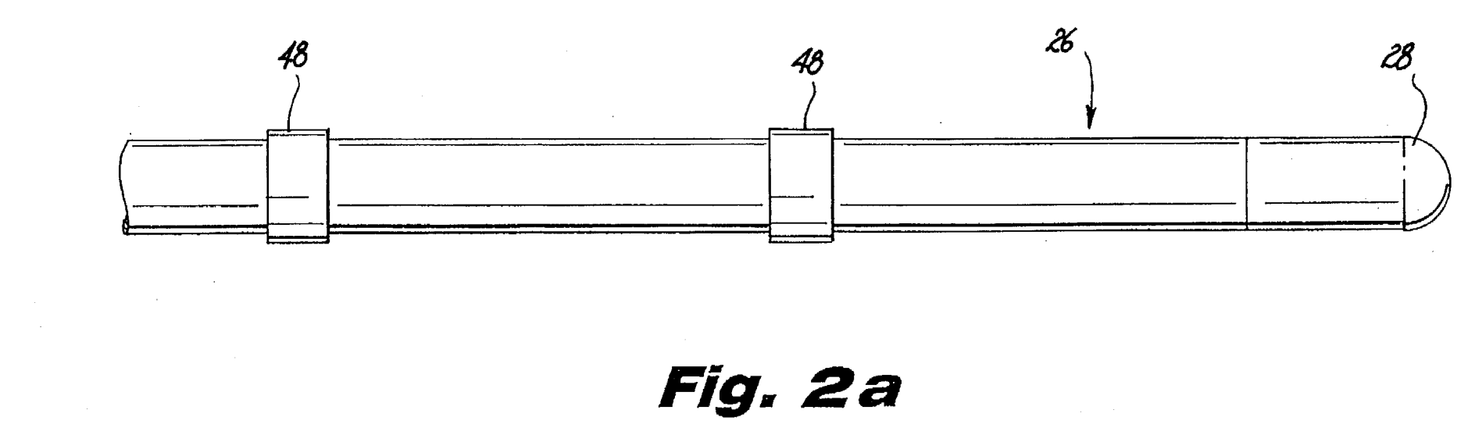
FIG. 2a illustrates the electrodes raised above the outer surface of the flexible tip assembly of FIG. 2.
Figure 2B:
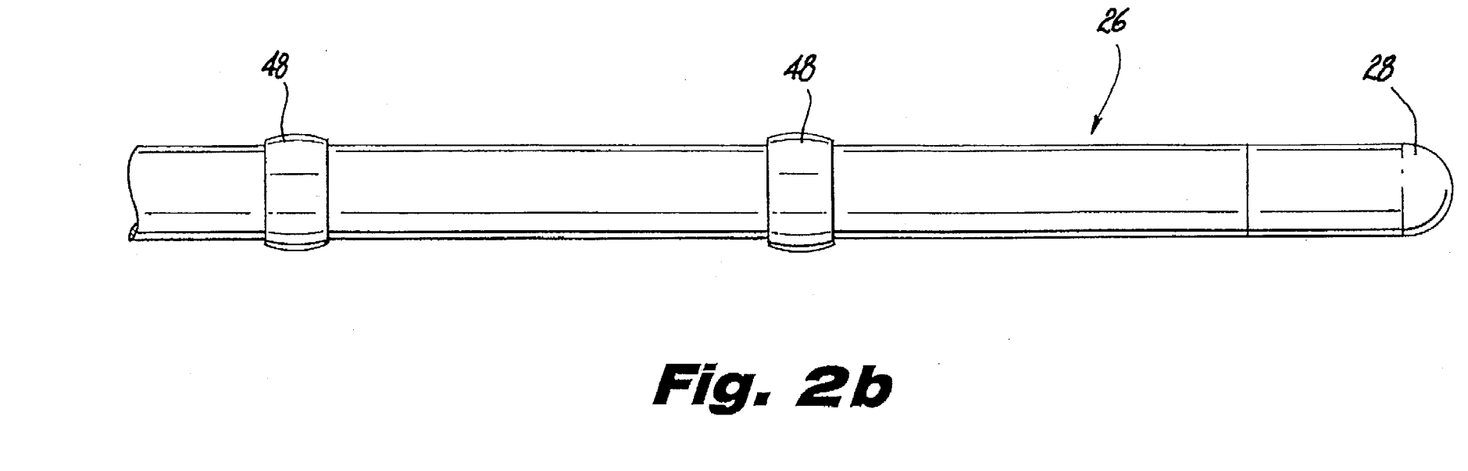
FIG. 2b illustrates the electrodes of a FIG. 2a being of a convex shape.

The flexible tip assembly 26 also contains a plurality of ring electrodes 48 spaced along the its outer surface. FIGS. 3 and 14 show a tip assembly 26 comprising three ring electrodes 48. Preferably, the ring electrodes 48 are raised above the outer surface of the flexible tip assembly 26 (as shown in FIG. 2a) to enhance the contact with the electrodes 48. A convex-shaped electrode (as shown in FIG. 2b) may also be used to achieve the same enhanced contact features. The ring electrodes contacts are electrically connected to respective signal wires 46.

Figure 10:
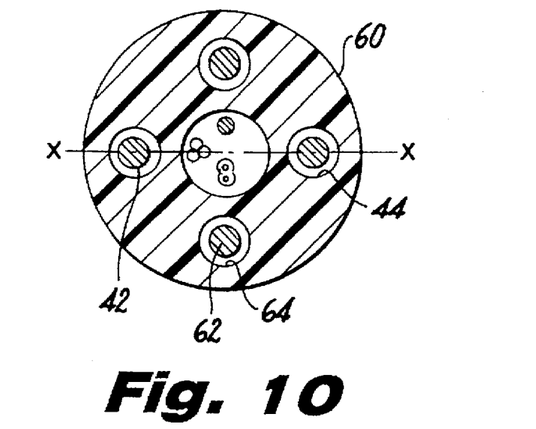
Figure 11:
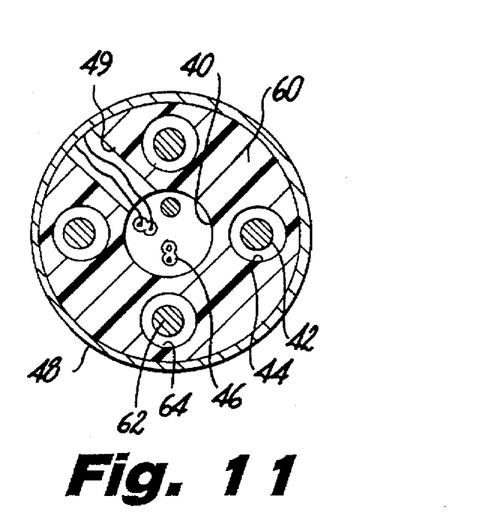

The signal wires 46 extend through the central lumen 40, from a location proximal to the handle/actuator 24 where they are connected to a connector 70 (FIG. 1) which enables the ring electrodes 48, the distal electrode cap 50, and the thermistor 52 to be easily coupled electrically to the recording equipment (not shown). The signal wires 46 extend distally through the central lumen 40 through the elongated shaft 22, the flexible tip assembly 26 and, in the case of the signal wires connected to the electrode cap 50 and the thermistor 52, through to the distal tip of the catheter 20. As illustrated in FIGS. 10–12, there is one signal wire 46 dedicated to each ring electrode 48. Each signal wire 46 is routed from the central lumen 40 within the flexible tip assembly 26, through a passageway 49 to their respective electrode 48 (FIGS. 11 and 12). The signal wires 46 are preferably electrically insulated from each other and, therefore, may all share a single central lumen 40 as shown in FIGS. 4–13.

Referring to FIGS. 3 and 14, the flexible tip assembly 26 terminates distally in a distal electrode assembly 28. The distal electrode assembly 28 comprises a threaded core 72, the pull cables 42, and an electrode cap 50 and thermistor 52 with their corresponding signal wires 46. The distal electrode assembly 28 is also coaxially aligned with the shaft 22 and the tip assembly 26.

The threaded core 72 is secured to the distal end of the tip assembly 26 to retain the distal electrode cap 50 as illustrated in FIGS. 3 and 14. The distal electrode cap 50 includes a hollow threaded recess 74 which engages the external threads of the threaded core 72. The remaining signal wires 46 running through the central lumen 40 are for the distal electrode cap 50 and the thermistor 52. Each signal wire 46 is connected to its respective electrode (ring or distal electrode cap 50) in a conventional manner, for example, by soldering or welding. The electrodes 48 provide signal information on heart potentials to remote recording equipment (not shown) used by the electrophysiologist. The thermistor 52 is similarly attached to its signal wire 46, and is primarily used for RF ablation.

As shown in FIGS. 3, 13 and 14, the threaded core 72 houses two pull cable lumens 45 and two reinforcement lumens 65. Each pull cable 42 extends out of the distal end of its pull cable lumen 45, and then is threaded into an adjacent empty reinforcement lumen 65. The distal end of each pull cable 42 is then adhesively bonded inside the reinforcement lumen 64. Preferably, the entire distal electrode assembly 28 is filled with an adhesive 76 to also facilitate bonding the distal electrode cap 50 to the threaded core 72.

The handle/actuator 24 has been fully disclosed in U.S. Pat. No. 5,383,852 to Stevens-Wright, and is incorporated by reference herein. According to the present invention, only two pull cables 42 are used, allowing for bidirectional movement in a single plane (FIG.2). The proximal ends of the pull cables 42 are preferably attached to a slider mechanism 80 (FIGS. 1 and 15a–c). Alternatively, the proximal ends of the pull cables 42 may be attached to the thumbwheel assembly 82 (not shown). In yet another embodiment, the proximal ends of each pull cable 42 may be attached to one of the slider mechanism 80 or the thumbwheel assembly 82. In such a configuration, the thumbwheel 82 may be used to provide for movement in a first direction, while the slider mechanism 80 may be used to provide movement in a second direction, all within a single plane.

Catheter Assembly

The following section describes the catheter assembly. Preferred materials, relative dimensions, and hardness characteristics are disclosed for the structure illustrated in FIGS. 1 and 3–14.

The elongated shaft 22 may be an extruded polyether block amide of the type sold by Atochem North America, Inc. under the trademark PEBAX (hardness 72–63 Shore D). A typical length is about 110–120 cm with an outer diameter of 0.092 inch (7 French). Alternatively, the elongated shaft 22 may be made of PELLETHANE urethane elastomer supplied by Dow Chemical Company. The outer diameter of the elongated shaft 22 is preferably 0.092 inch, whereas the inner diameter in preferably 0.060 inch.

The flexible tip assembly 26 is also an extrusion and may be made of PELLETHANE elastomer (hardness 90 Shore A) or of an extruded polyether block amide of the type sold by Atochem North America, Inc. under the trademark PEBAX (hardness 40–55 Shore D). Its length may be 2.0–8.0 cm.

The pull cables 42 may each comprise a multiplicity of ultra-high molecular weight polyethylene filaments, each forming a bundle with a diameter in the range of 0.003–0.004 inches. In the preferred embodiment of the invention, the pull cables are made from standed stainless steel cables. The protective sheath 33 surrounding the pull cables 42 may be made of TEFLON brand polytetrafluoroethylene manufactured by E.I. DuPont de Nemours & Co., Inc. of Wilmington, Del. The protective sheath 33 has an outer diameter of 0.014 inch and an inner diameter of 0.010 inch.

According to the invention, the reinforcement members 62 are preferably made from Nitinol, a Nickel-Titanium alloy, or from another super-elastic alloy displaying similar hysteritic stress/strain characteristics.

The threaded core 72 may be a polycarbonate or ABS plastic. It may be bonded to the distal end of the tip assembly 26 by an adhesive or by thermal bonding.

The electrodes 48 and 50 may be made of any appropriate electrode contact metal, such as platinum.

To assemble the catheter, the signal wires 46 are welded to the ring electrodes 48. The distal end of the flexible tip assembly 26 is tapered and the proximal end of the flexible tip assembly 26 is ground to a diameter of approximately 0.058 inch. The passage ways 49 for the signal wires 46 are formed in the flexible tip assembly 26 and that section is pulled to reduce its diameter so the electrodes rings 48 can slide into position. The signal wires 46 are then threaded through the passage ways 49. The tapered end is then cut to length and cored to a predetermined diameter. The ground proximal end of the flexibly tip assembly 26 is then inserted into the cored distal end of elongated shaft 22 and thermally bonded thereto. The reinforcement members 62 are then inserted into their respective lumens 64 within the flexible tip assembly 26.

Figure 4:
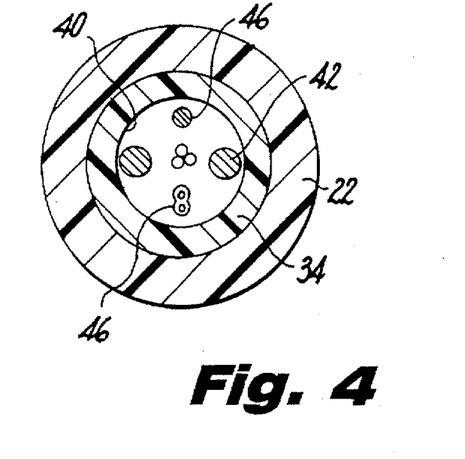
FIGS. 4–13 are transverse sections along lines 5—5 through 13—13.
Figure 5:
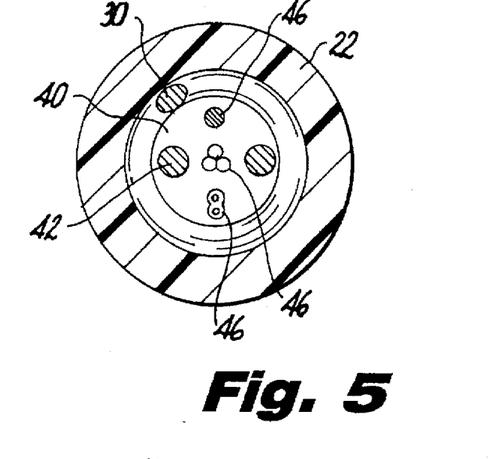
Figure 6:
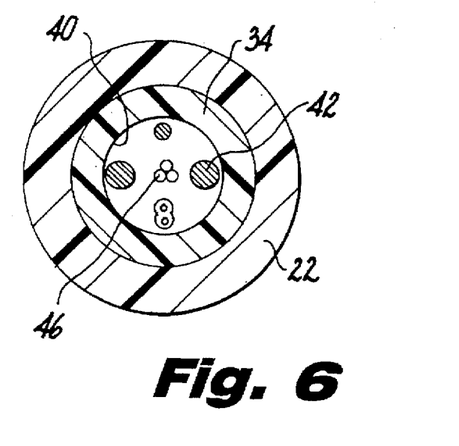

The spring 30, encapsulated by an outer protective sheath 32, is inserted inside the elongated shaft 22. The spring 30 surrounds the central lumen 40. At both ends of the spring 30, spring stops 34 *a* and *b* are employed to prevent longitudinal travel of the spring 30. The two spring stops 34*a* and *b* (one at either end of the spring) are thermally bonded to the inner surface of the elongated shaft 22 (FIGS. 4 and 6). As shown in FIG. 3, the distal spring stop 34*b* terminates distally approximately 4 mm from the distal end of the elongated shaft 22. This allows for the ground proximal portion of the flexible tip assembly 26 to be readily inserted into the elongated shaft 22.

The pull cables 42 are conditioned to rid them of "creep" and stretch. This is done by cyclically loading the pull cables 42 by the application of a specified tensile force. By using stainless steel pull cables 42, the possibility of "creep" and stretch is greatly reduced. The cables 42 are then properly positioned within the elongated shaft 22 and threaded through their respective lumens 44 at the proximal portion of the flexible distal tip 26 and distally through the flexible tip assembly 26. The pull cables 42 are then inserted into the cable lumens 45 within the threaded core 72. As shown in FIGS. 3 and 13, the pull cables 42 are then threaded back through an adjacent reinforcement lumen 65 within the threaded core 72. The distal end of the pull cables 42 are fixably attached within the reinforcement lumen 65 at a location distal to the reinforcement member 62. One preferable method for attaching the pull cables 42 to the distal tip of the catheter 20 is to completely fill the hollow recess within the distal electrode cap 50 with an adhesive, thereby adhesively attaching the pull cables 42 within the distal electrode assembly 28.

The distal electrode cap 50 is screwed onto the threaded core 72. The entire distal electrode assembly 28 is then thermally bonded to the flexible tip assembly 26. The assembled catheter 20 with the signal wires 46 and pull cables 42 extending from the proximal end of the catheter 20, may then be attached to the handle/actuator 24, as described in U.S. Pat. No. 5,383,852.

While the invention has been particularly shown and described with reference to a preferred embodiment thereof, it will be understood by those skilled in the art that various changes in form and details may be made therein without departing from the spirit and scope of the invention.

What is claimed is:

1. A bidirectional steering catheter comprising:
    a distal electrode assembly having a distal end and a proximal end;
    a flexible tip assembly attached to the proximal end of the distal electrode assembly;
    an elongated shaft having a distal and proximal end, the distal end of the elongated shaft attached to the flexible tip assembly, and the elongated shaft having a central lumen running the length of the shaft;
    a handle/actuator attached to the proximal end of the elongated shaft;
    at least two pull cables having first and second ends, each pull cable being attached at its first end to the handle/actuator and extending distally through the central lumen within the elongated shaft and the flexible tip assembly, each pull cable being further attached at its second end to the distal electrode assembly, such that the distal electrode assembly may be moved between a first and a second position within a single plane by manipulating the handle/actuator; and
    at least two reinforcement members located inside the flexible tip assembly, wherein each reinforcement member has a proximal section, a middle section and a distal section, the proximal section being of greater stiffness than the middle section, such that the length of each reinforcement member has a variable stiffness that distributes stresses evenly along the length of the tip assembly.

2. The bidirectional steering catheter as in claim 1, further comprising:
    a plurality of ring electrodes attached to an outer surface of the flexible tip assembly; and a plurality of signal wires running the length of the catheter, one signal wire being attached to each ring electrode.

3. The bidirectional steering catheter as in claim 2, wherein the plurality of ring electrodes are raised above the outer surface of the flexible tip assembly, for enhanced electrode contact.

4. The bidirectional steering catheter as in claim 2, wherein the plurality of ring electrodes are convexly shaped for enhanced electrode contact.

5. The bidirectional steering catheter as in claim 2, further comprising a thermistor located within the distal electrode assembly, the thermistor being electrically connected to one of the signal wires.

6. The bidirectional steering catheter as in claim 2, further comprising an electrode cap located at the distal end of the distal electrode assembly, and being electrically connected to one of the signal wires.

7. The bidirectional steering catheter as in claim 1, wherein each pull cable is made from ultra-high molecular weight polyethylene.

8. The bidirectional steering catheter as in claim 1, wherein each pull cable is made from a stranded stainless steel cable.

9. The bidirectional steering catheter as in claim 1, wherein each pull cable is enclosed in a protective sheath.

10. The bidirectional steering catheter as in claim 9, wherein the protective sheath is made from polytetrafluoroethylene.

11. The bidirectional steering catheter as in claim 10, further comprising two pull cable lumens located within the flexible distal assembly, through which the two pull cables are inserted.

12. The bidirectional steering catheter as in claim 1, wherein the proximal and distal sections of each reinforcement member are of equal diameter, whereas the middle section has a smaller diameter, thereby imparting variable stiffness to the flexible tip assembly.

13. The bidirectional steering catheter as in claim 12, wherein each reinforcement member is made from a superelastic alloy.

14. The bidirectional steering catheter as in claim 13, wherein each reinforcement member is made from Nitinol, a Nickel-Titanium alloy.

15. The bidirectional steering catheter as in claim 13, further comprising two reinforcement lumens located within the flexible tip assembly, through which the two reinforcement members are inserted.

16. The bidirectional steering catheter as in claim 15, wherein the diameter of the proximal and distal sections of each reinforcement member is substantially equal to the diameter of the reinforcement lumen, resulting in a tight fit around the reinforcement member, thereby anchoring the reinforcement member within the reinforcement lumen.

17. A bidirectional steering catheter comprising:

a distal electrode assembly having a distal and a proximal end;

a flexible tip assembly attached to the proximal end of the distal electrode assembly, the flexible tip assembly including a tubular section, through which two reinforcement lumens and two pull cable lumens are embedded, and further including a central lumen running the length of the flexible tip assembly, the central lumen having a plurality of signal wires running through the center thereof;

a plurality of ring electrodes attached to a surface of the flexible tip assembly, each ring electrodes being electrically connected to one of the signal wires;

a distal electrode cap attached to the distal end of the distal electrode assembly and being electrically connected to one of the signal wires;

a thermistor attached to the distal end of the distal electrode assembly and being electrically connected to one of the signal wires;

an elongated shaft having a distal and proximal end, the distal end of the elongated shaft attached to the flexible tip assembly, and the elongated shaft having the central lumen running the length of the shaft;

a handle/actuator attached to the proximal end of the elongated shaft;

two pull cables, each having a first end and a second end, each pull cable being attached at its first end to the handle/actuator and extending distally through the central lumen within the elongated shaft and through the pull cable lumens within the flexible tip assembly, each pull cable further being attached at its second end to the distal electrode assembly, such that the distal electrode assembly may be moved between a first and a second position within a single plane by manipulating the handle/actuator; and at least two reinforcement members located inside the reinforcement lumens of the flexible tip assembly, wherein each reinforcement member has a proximal section, a middle section and a distal section, the proximal section being of greater stiffness than the middle section, such that the length of each reinforcement member has a variable stiffness that distributes stresses evenly along the length of the tip assembly.

18. The bidirectional steering catheter as in claim 17, wherein the plurality of ring electrodes are raised above the surface of the flexible tip assembly, for enhanced electrode contact.

19. The bidirectional steering catheter as in claim 17, wherein the plurality of ring electrodes are convexly shaped for enhanced electrode contact.

20. The bidirectional steering catheter as in claim 17, wherein each pull cable is enclosed in a protective sheath.

21. The bidirectional steering catheter as in claim 17, wherein the protective sheath surrounding each pull cable is made from polytetrafluoroethylene.

22. The bidirectional steering catheter as in claim 17, wherein the proximal and distal sections of each reinforcement member are of equal diameter, whereas the middle section has a smaller diameter, thereby imparting variable stiffness to the flexible tip assembly.

23. The bidirectional steering catheter as in claim 22, wherein each reinforcement member is made from a superelastic alloy.

24. The bidirectional steering catheter as in claim 23, wherein each reinforcement member is made from Nitinol, a Nickel-Titanium alloy.

25. The bidirectional steering catheter as in claim 24, wherein the diameter of the proximal and distal sections of each reinforcement member is substantially equal to the diameter of the reinforcement lumen, resulting in a tight fit around the reinforcement member, thereby anchoring the reinforcement member within the reinforcement lumen.

* * * * *